(12) United States Patent
Ross et al.

(10) Patent No.: US 8,568,425 B2
(45) Date of Patent: Oct. 29, 2013

(54) WIRE SPOOL FOR PASSING OF WIRE THROUGH A ROTATIONAL COUPLING

(75) Inventors: Adam J. Ross, Prospect, CT (US); Michael A. Zemlok, Prospect, CT (US)

(73) Assignee: Covidien LP, Mansfield, MA (US)

( * ) Notice: Subject to any disclaimer, the term of this patent is extended or adjusted under 35 U.S.C. 154(b) by 302 days.

(21) Appl. No.: 13/217,407

(22) Filed: Aug. 25, 2011

(65) Prior Publication Data
US 2012/0109154 A1 May 3, 2012

Related U.S. Application Data

(60) Provisional application No. 61/408,800, filed on Nov. 1, 2010.

(51) Int. Cl.
*A61B 17/17* (2006.01)
(52) U.S. Cl.
USPC ............. 606/139; 606/1; 606/27; 606/32; 606/142; 227/175.1
(58) Field of Classification Search
None
See application file for complete search history.

(56) References Cited

U.S. PATENT DOCUMENTS

| | | | |
|---|---|---|---|
| 5,084,057 A | 1/1992 | Green et al. | |
| 5,100,420 A | 3/1992 | Green et al. | |
| 5,465,894 A * | 11/1995 | Clark et al. | 227/175.1 |
| 5,607,436 A | 3/1997 | Pratt et al. | |
| 5,695,502 A | 12/1997 | Pier et al. | |
| 6,817,508 B1 | 11/2004 | Racenet et al. | |
| 2008/0046122 A1 | 2/2008 | Manzo | |
| 2008/0255607 A1 | 10/2008 | Zemlok | |
| 2009/0145947 A1 | 6/2009 | Scirica et al. | |
| 2009/0179063 A1 | 7/2009 | Milliman et al. | |
| 2012/0078247 A1 * | 3/2012 | Worrell et al. | 606/45 |
| 2012/0078248 A1 * | 3/2012 | Worrell et al. | 606/45 |

FOREIGN PATENT DOCUMENTS

| | | |
|---|---|---|
| EP | 1980213 A2 | 10/2008 |
| EP | 1980215 A2 | 10/2008 |
| EP | 2055243 A2 | 5/2009 |

OTHER PUBLICATIONS

European Search Report for corresponding EP11250782 date of mailing is Feb. 27, 2012 (3 pgs).

* cited by examiner

*Primary Examiner* — Melanie Tyson
*Assistant Examiner* — Todd J Scherbel

(57) ABSTRACT

A surgical apparatus for performance of a surgical procedure on body tissue is provided and includes a housing, an elongate tubular member, a drive assembly, an electrical coupling component, and an electrical wire. The elongate tubular member is at least partially supported by the housing and defines a center lumen and a longitudinal axis. The drive assembly extends from the housing into the center lumen of the elongate tubular member. The electrical coupling component is located about the drive assembly. The electrical wire extends from within the housing into the elongate tubular member. The electrical wire is wrapped about the electrical coupling component, which allows the elongate tubular member to rotate about the longitudinal axis while allowing the electrical wire to be fixed within the housing and the elongate tubular member.

19 Claims, 10 Drawing Sheets

WIRE SPOOL FOR PASSING OF WIRE THROUGH A ROTATIONAL COUPLING

CROSS REFERENCE TO RELATED APPLICATION

The present application claims the benefit of and priority to U.S. Provisional Application Ser. No. 61/408,800 filed on Nov. 1, 2010, the entire contents of which are incorporated herein by reference.

BACKGROUND

1. Technical Field

The present disclosure relates to articulating and rotating surgical instruments. More specifically, the present disclosure relates to a coupling that allows articulation and rotation of an endoscopic portion of a surgical instrument, such as a clip applier, a surgical stapler and the like.

2. Background of Related Art

Endoscopic staplers and clip appliers are known in the art and are used for a number of distinct and useful surgical procedures. In the case of a laparoscopic surgical procedure, access to the interior of an abdomen is achieved through narrow tubes or cannulas inserted through a small entrance incision in the skin. Minimally invasive procedures performed elsewhere in the body are often generally referred to as endoscopic procedures. Typically, a tube or cannula device is extended into the patient's body through the entrance incision to provide an access port. The port allows the surgeon to insert a number of different surgical instruments therethrough using a trocar and for performing surgical procedures far removed from the incision.

During a majority of these procedures, the surgeon must often terminate the flow of blood or another fluid through one or more vessels. The surgeon will often apply a surgical clip to a blood vessel or another duct to prevent the flow of body fluids therethrough during the procedure. An endoscopic clip applier is known in the art for applying surgical clips during an entry to the body cavity. Such surgical clip appliers are typically fabricated from a biocompatible material and are usually compressed over a vessel. Once applied to the vessel, the compressed clip terminates the flow of fluid therethrough.

Endoscopic clip appliers that are able to apply multiple clips in endoscopic or laparoscopic procedures during a single entry into the body cavity are described in commonly-assigned U.S. Pat. Nos. 5,084,057 and 5,100,420 to Green et al., which are both incorporated by reference in their entirety. Another multiple endoscopic clip applier is disclosed in commonly-assigned U.S. Pat. No. 5,607,436 to Pratt et al., the contents of which is also hereby incorporated by reference herein in its entirety. These devices are typically, though not necessarily, used during a single surgical procedure. U.S. Pat. No. 5,695,502 to Pier et al., the disclosure of which is hereby incorporated by reference herein, discloses are sterilizable surgical clip applier. The clip applier advances and forms multiple clips during a single insertion into the body cavity.

Surgical fastening devices wherein tissue is first grasped or clamped between opposing jaw structure and then joined by surgical fasteners are also well known in the art. The fasteners are typically in the form of surgical staples, but two-part polymeric fasteners can also be utilized.

Instruments for this purpose can include a tool assembly with two elongated members which are respectively used to capture or clamp tissue. Typically, one of the members carries a staple cartridge which houses a plurality of staples arranged, for example, in at least two lateral rows while the other member has an anvil that defines a surface for forming the staple legs as the staples are driven from the staple cartridge. In some staplers, the stapling operation is effected by cam bars that travel longitudinally through the staple cartridge, with the cam bars acting upon staple pushers for sequentially ejecting the staples from the staple cartridge.

Endoscopic or laparoscopic procedures are often performed remotely from the incision. Consequently, application of clips or fasteners may be complicated by a reduced field of view or reduced tactile feedback for the user at the proximal end of the device. It is therefore desirable to improve the operation of the instrument by providing an instrument that is capable of articulating and rotating for better application of the surgical clips.

SUMMARY

A surgical apparatus for performance of a surgical procedure on body tissue is provided and includes a housing, an elongate tubular member, a drive assembly, an electrical coupling component, and an electrical wire. The elongate tubular member is at least partially supported by the housing and defines a center lumen and a longitudinal axis. The drive assembly extends from the housing into the center lumen of the elongate tubular member. The electrical coupling component is located about the drive assembly. The electrical wire extends from within the housing into the elongate tubular member. The electrical wire is wrapped about the electrical coupling component, which allows the elongate tubular member to rotate about the longitudinal axis while allowing the electrical wire to be fixed within the housing and the elongate tubular member.

The surgical apparatus may include an electrical component connected with the elongate tubular member.

The surgical apparatus may include a limiting mechanism to restrict rotational movement of the elongate tubular member. The limiting mechanism includes an inner band and an outer collar and a ball bearing. The inner band defines a spiral cam slot and the outer collar defines a longitudinal cam slot. The ball bearing is located within both the spiral cam slot and the longitudinal cam slot. The spiral cam slot may traverse about the inner band about 700°. A neutral decent may be defined midway along the longitudinal cam slot to provide a tactile indication of a neutral position of the elongate tubular member. The elongate tubular member is prevented from further rotation by the ball bearing acting against either a proximal end or a distal end of the longitudinal cam slot.

The electrical coupling component includes a fixed member and a rotatable member. The fixed member is prevented from both longitudinal and rotational movement by the housing. The rotatable member is rotatable with respect to both the fixed member and the housing. The rotatable member includes a tubular spool. The tubular spool may define a helical groove to provide the electrical wire with a predefined path along the tubular spool.

The fixed member may define a first passageway providing a path for the electrical wire through the fixed member. The rotatable member may define a second passageway providing a path for the electrical wire through the rotatable member.

In another embodiment, a surgical apparatus for performance of a surgical procedure on body tissue is provided and includes a housing, an elongate member, an electrical coupling interface, and a wire. The elongate member is rotationally connected with the housing. The electrical coupling interface has a fixed member and a rotatable member. One of the fixed member and the rotatable member has a spool extending therefrom. The spool is in connection with the other of the fixed and rotatable member. The wire has a first portion, a second portion, and a third portion. The first portion of the wire is in a fixed position with respect to the housing. The second portion of the wire is wrapped about the spool. The third portion of the wire is restrained with respect to the elongate member.

The fixed member is prevented from both longitudinal and rotational movement by the housing. The rotatable member is rotatable with respect to both the fixed member and the housing.

The surgical apparatus may include a drive assembly at least partially supported by the housing. The drive assembly is at least partially positioned within the electrical coupling interface.

In another embodiment, a rotational interface assembly for interconnecting an operating end of a device and a working end of the device is provided and includes a spool, a retaining member and a wire. The retaining member is able to restrict axial movement of the spool while allowing rotational movement of the spool. The wire has a first portion, a second portion, and a third portion. The first portion of the wire is in a fixed position with respect to the operating end of the device. The second portion of the wire is wrapped about the spool. The third portion of the wire is restrained with respect to the working end of the device.

BRIEF DESCRIPTION OF THE DRAWINGS

The present clip applier will be more fully appreciated as the same becomes better understood from the following detailed description when considered in connection with the following drawings, in which.

Figure 1:
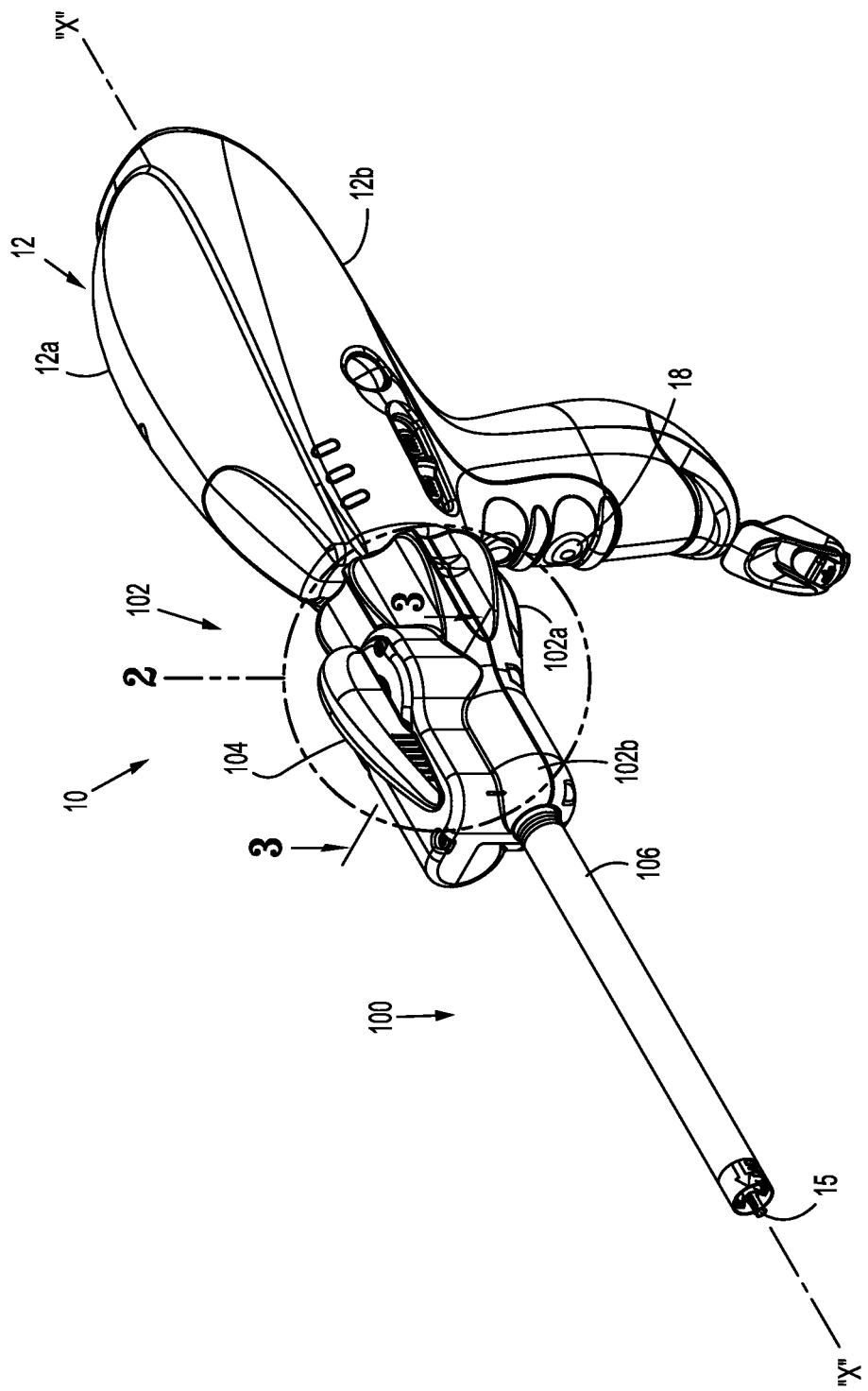
FIG. 1 is a front, perspective view of a surgical instrument according to an embodiment of the present disclosure.

Other features of the present disclosure will become apparent from the following detailed description, taken in conjunction with the accompanying drawings, which illustrate, by way of example, the principles of the present disclosure.

DETAILED DESCRIPTION OF EMBODIMENTS

Embodiments of surgical instruments in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

Referring now to the drawings, wherein like reference numerals identify identical or similar structural elements of the subject device through out the several views, there is illustrated in FIGS. 1-13, a surgical instrument, designated generally by reference numeral 10. U.S. patent application Ser. No. 11/786,933, filed on Apr. 13, 2007, the entire content of which is incorporated herein by reference, describes in detail the structure and operation of an exemplary surgical instrument that may incorporate or be used with the presently disclosed adapter assembly.

Figure 1A:
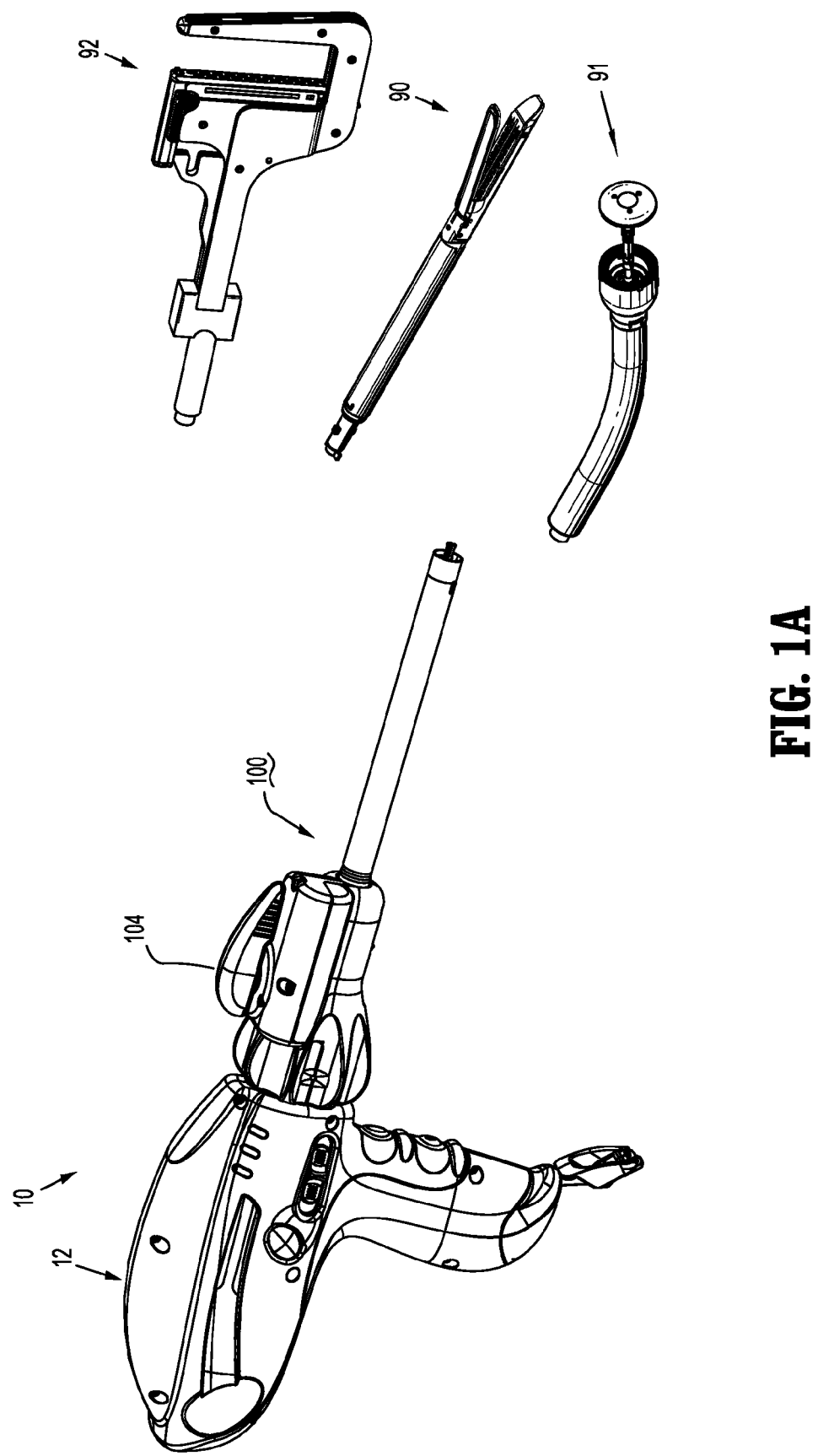
FIG. 1A is a front, perspective view of a surgical instrument according to an embodiment of the present disclosure with a variety of end effectors.

As seen in FIGS. 1 and 1A, a rotational interface 100 is shown connected with or otherwise supported on surgical instrument 10. Surgical instrument 10 includes a housing 12, at least one drive assembly 14 and at least one energy source for powering the at least one drive motor (not shown for clarity).

As seen in FIG. 1A, rotational interface 100 is configured and adapted to operatively interconnect and couple any one of a number of end effectors to surgical instrument 10. For example, rotational interface 100 is configured and adapted to operatively interconnect and couple an endo-gastrointestinal anastomosis end effector 90, an end-to-end anastomosis end effector 91, or a transverse anastomosis end effector 92 to surgical instrument 10.

Reference may be made to U.S. Patent Publication No. 2009/0145947, filed Jan. 14, 2009, the entire content of which is incorporated herein by reference for a detailed discussion of the construction and operation of the endo-gastrointestinal anastomosis end effector 90.

Reference may be made to U.S. Patent Publication No. 2009/0179063, filed Mar. 20, 2009, the entire content of which is incorporated herein by reference for a detailed discussion of the construction and operation of the end-to-end anastomosis end effector 91.

Reference may be made to U.S. Pat. No. 6,817,508, issued Nov. 16, 2004, the entire content of which is incorporated herein by reference for a detailed discussion of the construction and operation of the transverse anastomosis end effector 92.

Figure 2:
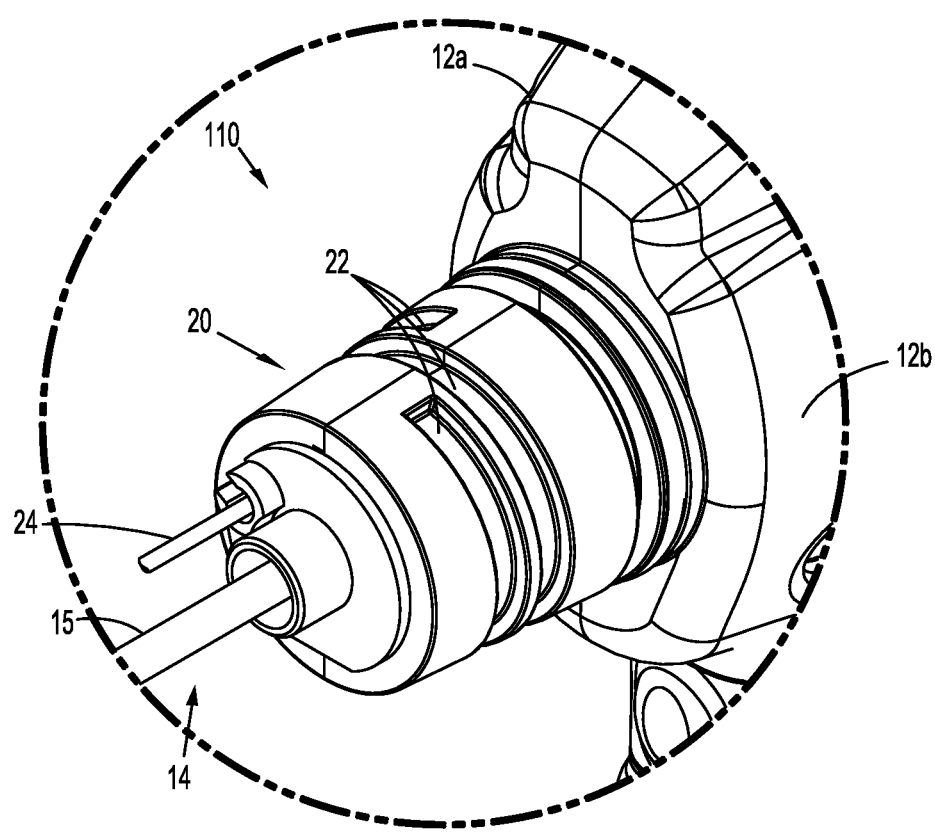
FIG. 2 is an enlarged perspective view of the indicated area of detail of FIG. 1 with the articulation dial cover portions removed for clarity.

As seen in FIG. 2, housing 12 of surgical instrument 10 supports the drive assembly 14. Drive assembly 14 includes a drive shaft 15 translatably, slidably, or rotatably supported between right side half-section 12a and left side half-section 12b of housing 12, for movement of the drive shaft 15 along or about a longitudinal 'X' axis of surgical instrument 10.

Each of the end effectors 90, 91, and 92 includes at least one axially translatable drive member therein that is connectable with the drive shaft 15, and that is configured and adapted to at least one of open and close the jaw assemblies by approximating or separating the anvil assembly and the cartridge assembly to/away from one another, and to fire the end effector to expel staples contained in the cartridge assembly for formation against the anvil assembly and possibly to actuate a knife blade along the staple line. Each of end effectors 90, 91, and 92 may further include an axially translatable drive member therein that is configured and adapted to cause an articulation of end effector 90, 91, and/or 92.

With continued reference to FIGS. 1 and 1A, a detailed description of the construction and operation of rotational interface 100 is provided. Rotational interface 100 includes a knob housing 102 configured and adapted to connect to a nose portion 20 (FIG. 2) of the housing 12. Knob housing 102 includes an articulation lever 104 mounted on the forward end of housing 12 to facilitate articulation of the drive assembly 14 with respect to the longitudinal 'X' axis. Knob housing 102 may be formed in a pair of knob housing halves, namely an upper knob housing half 102a and a lower knob housing half 102b. Rotational interface 100 further includes an outer tube 106 extending from a distal end of knob housing 102 along longitudinal 'X' axis. Knob housing 102 and outer tube 106 are configured and dimensioned to contain the components of rotational interface 100. Outer tube 106 may be dimensioned such that outer tube 106 may pass through a typical trocar port, cannula or the like. Knob housing 102 is secured to outer tube 106 in such a manner that rotation of knob housing 102 results in rotation of the outer tube 106.

Figure 3:
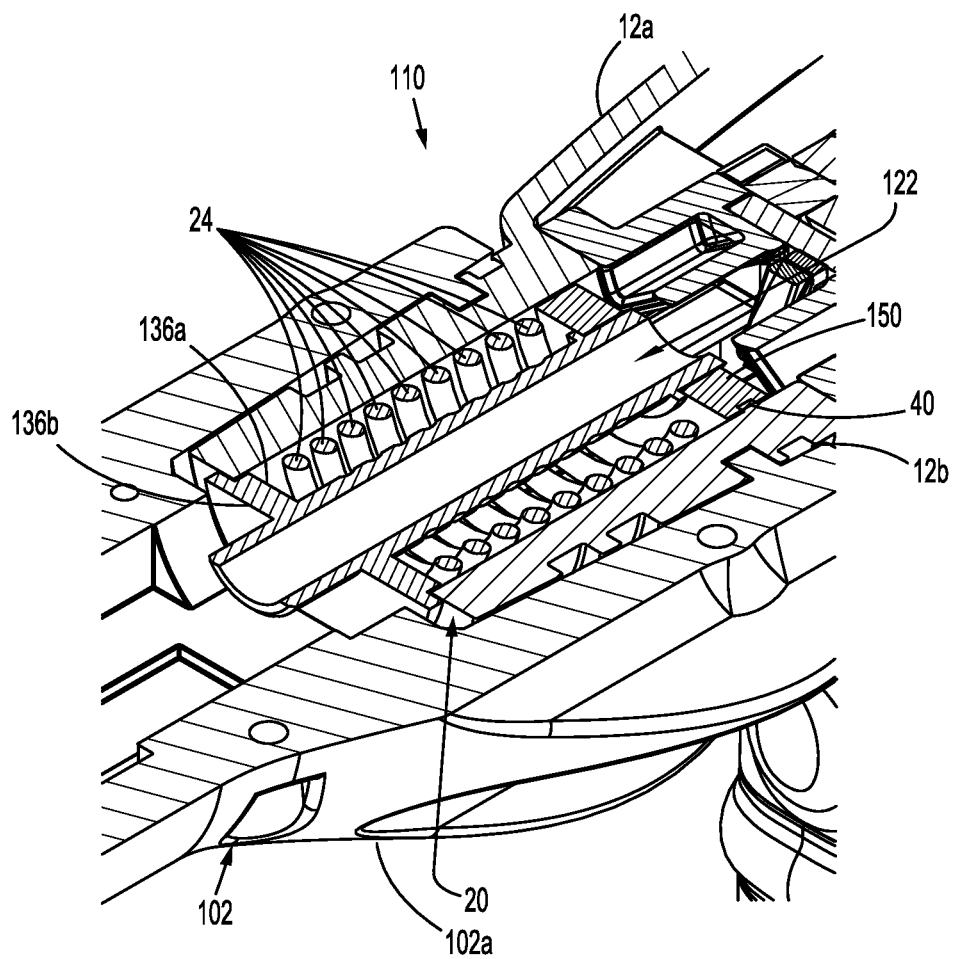
FIG. 3 is a cross-sectional view of the indicated area of detail of FIG. 1.
Figure 6:
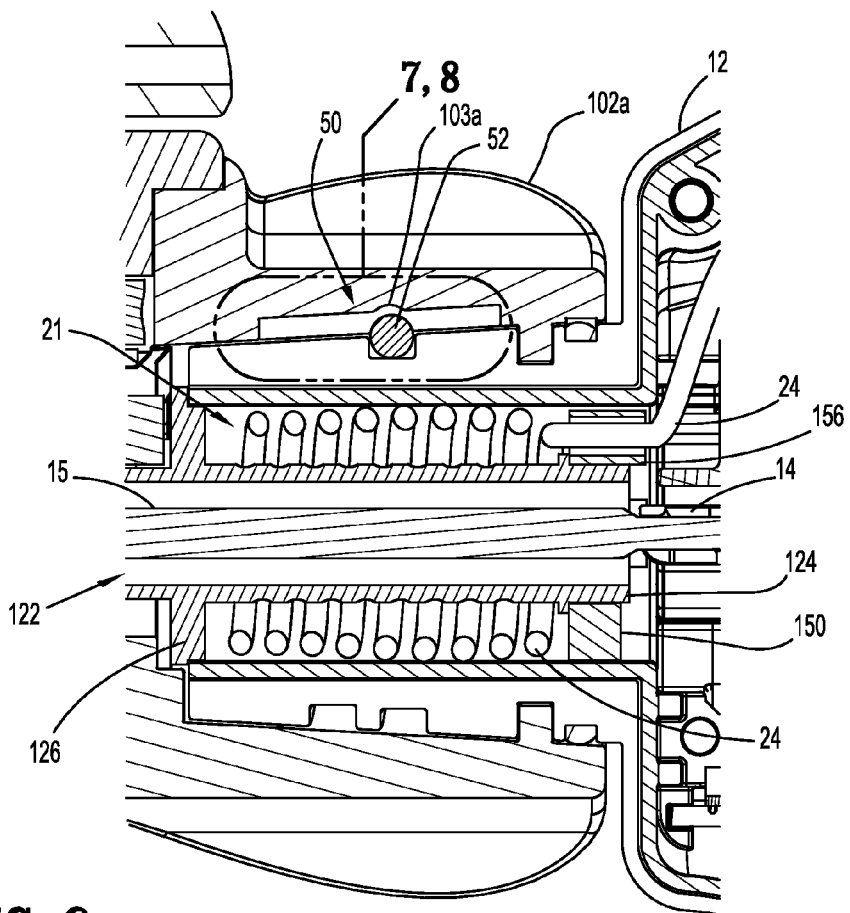
FIG. 6 is a longitudinal, cross-sectional view of the proximal portion of the articulation dial, shown in an neutral position.
Figure 7:
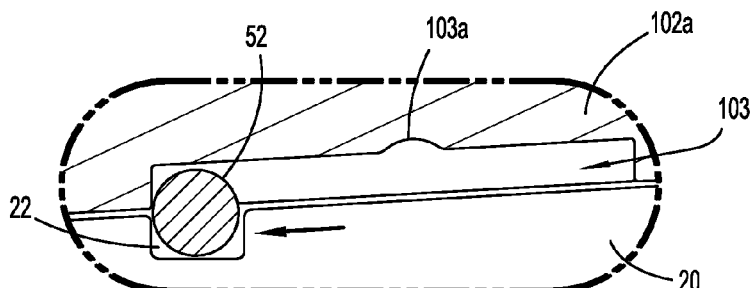
FIG. 7 is a longitudinal, cross-sectional view of the longitudinal recess area of the articulation dial, shown in an first extreme position.
Figure 8:
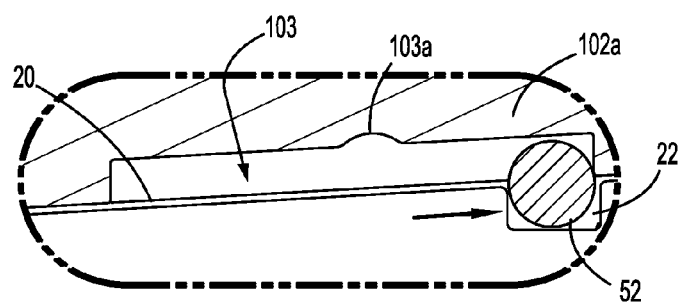
FIG. 8 is a longitudinal, cross-sectional view of the longitudinal recess area of the articulation dial, shown in a second extreme position.

As seen in FIGS. 2, 3, and 6, the nose portion 20 of the housing 12 defines a cylindrical passageway 21 that contains an electrical coupling assembly 110. The electrical coupling assembly 110 includes a spool 120 and a bushing 150 (See FIGS. 9 and 10). Electrical coupling assembly 110 allows passage of a portion of the drive shaft 15 through a center passage 122 in the spool 120. The bushing 150 is restrained by and is fixed with respect to the housing 12. The spool 120 has an elongate tubular portion 124 that is rotatably attached within the bushing 150.

Figure 9:
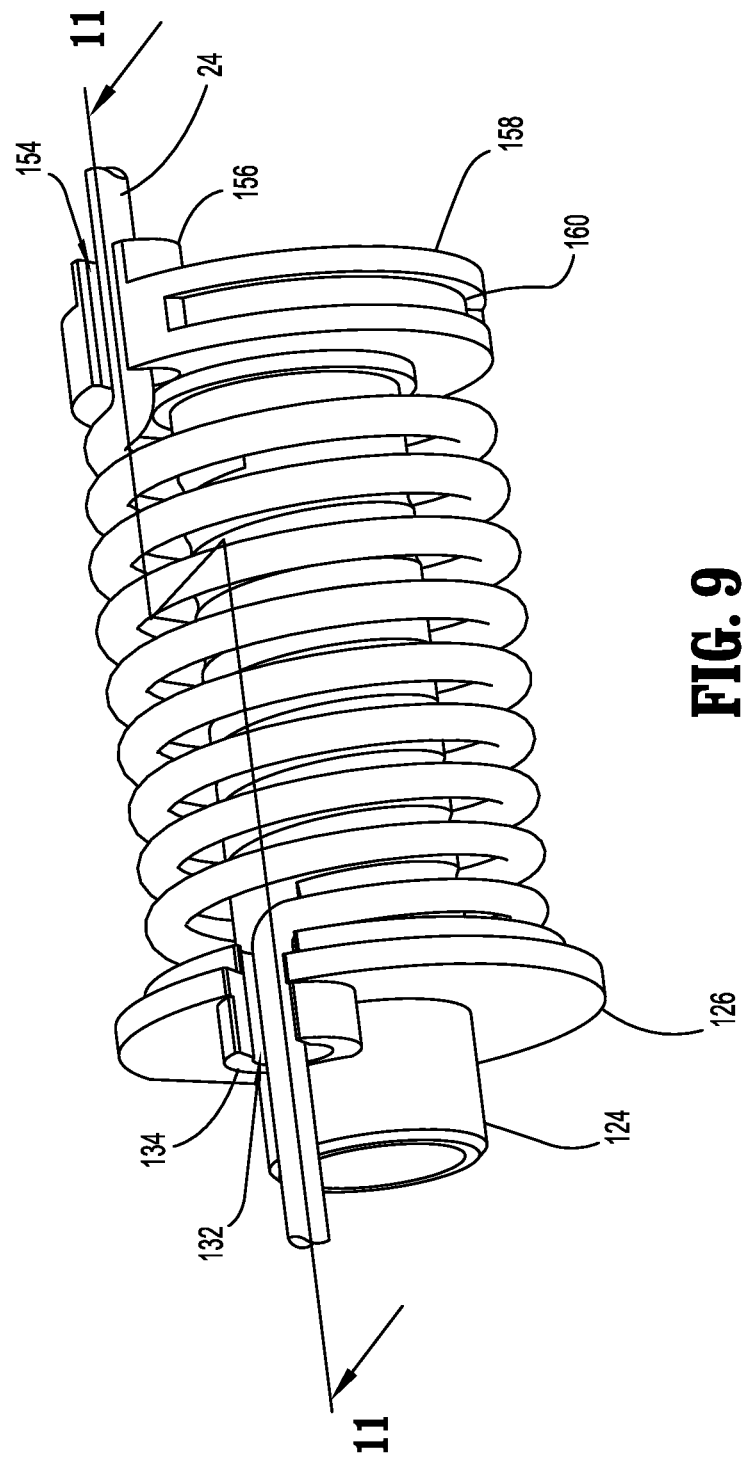
FIG. 9 is a front, perspective view of a wire spool coupling according to an embodiment of the present disclosure.
Figure 10:
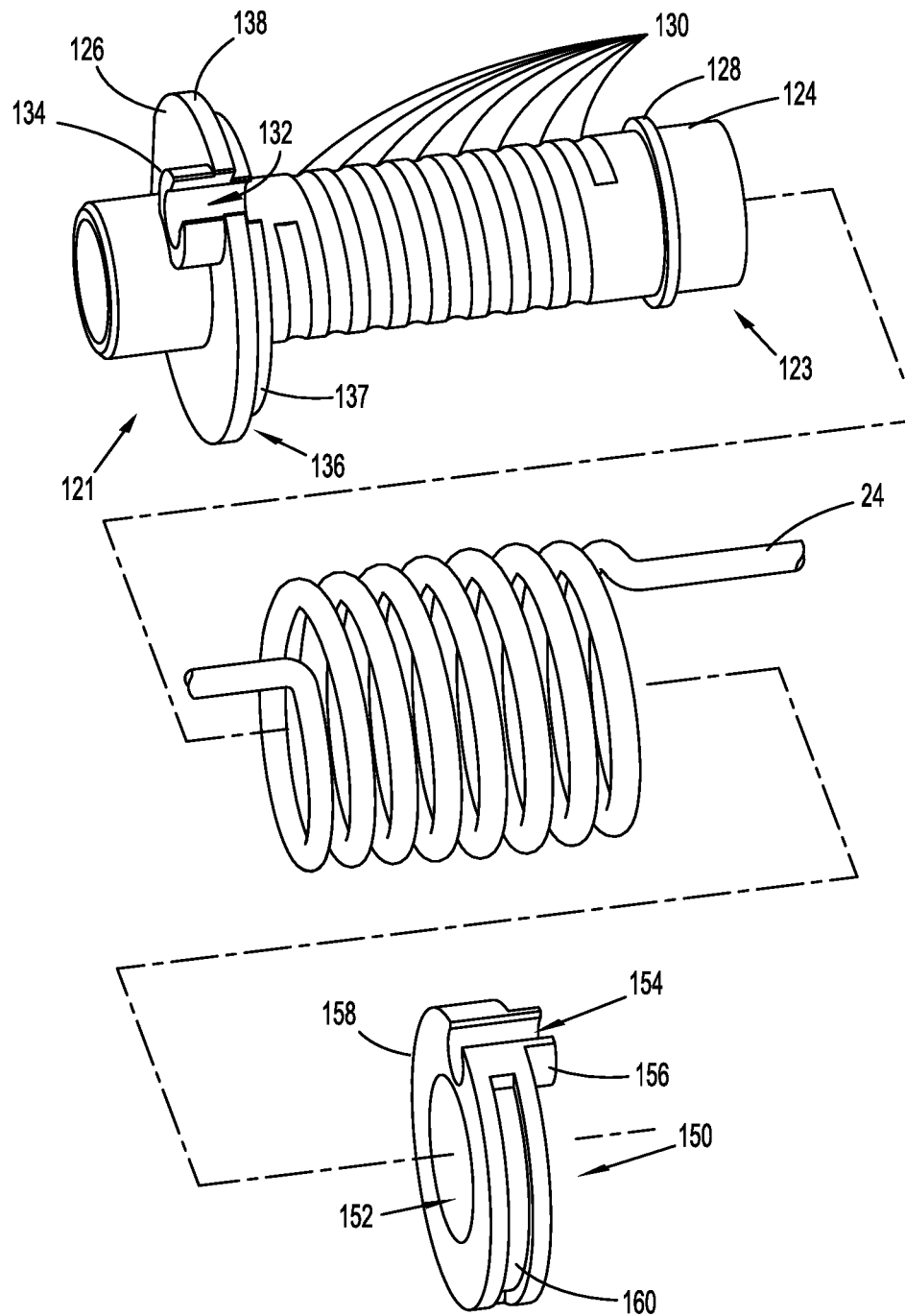
FIG. 10 is an exploded perspective view of the wire spool coupling of FIG. 9.

As seen in FIGS. 9 and 10, a distal portion 121 of the spool 120 includes a distal flange 126 extending radially outward from the elongate tubular portion 124. A proximal flange 128 extends about the proximal end 123 of the elongate tubular portion 124. Proximal flange 128 abuts against distal flange 126 and has a radius 137 that is relatively smaller than a radius 138 of distal flange 128. A helical recess 130 extends longitudinally about the elongate tubular portion 124 between the distal flange 126 and the proximal flange 128. The distal flange 126 defines a distal, longitudinally extending passageway or channel 132 through the distal flange 126. A distal boss 134 extends distally about the distal channel 132 from the distal flange 126. A shoulder 136 is defined by the difference of radius 137 and radius 138 of the distal flange 126. The radius 137 is sized to allow an inner portion 136a to fit inside cylindrical passageway 21 and an outer portion 136b to be slightly larger than the cylindrical passageway 21.

The bushing 150 has a center aperture 152 that is sized to receive the proximal portion 123 of the elongate tubular portion 124. The aperture 152 allows the bushing 150 to be placed about the elongate tubular portion 124 and slide up to the proximal flange 128. A proximal boss 156 extends proximally from the bushing 150. A proximal, longitudinally extending passageway or channel 154 is defined in an outer edge 158 of the bushing 15. A proximal boss 156 extends proximally about the proximal channel 154 of the bushing 150. A recessed circumferential channel 160 encircles at least a portion of the outer edge 158 of the busing 150.

As shown in FIGS. 3, 6, and 9-13, the surgical instrument 10 includes an electrical wire 24 having a first portion extending through the proximal channel 154 of the bushing 150, a second portion wrapped about the elongated tubular portion 124, and a third portion that extends distally through the distal channel 132 of distal flange 126.

With reference to FIG. 3, the bushing 150 is nested between the right side half section 12a and the left side half section 12b of the housing 12. At least one protrusion 40 extends from the nose portion 20 into the radial channel 160 of the bushing 150 to rotationally secure the bushing 150 in place relative to the nose portion 20 and to prevent longitudinal movement of the bushing 150.

As seen in FIGS. 3 and 6, the distal flange 126 of the spool 120 is rotatably interposed between the nose portion 20 of the housing 12 and the knob housing 102, allowing the spool 120 to rotate and preventing the spool 120 from moving along the longitudinal 'X' axis. The housing 12 prevents proximal movement of the spool 120 by the abutment of the shoulder 136 with the nose portion 20. Distal movement of the spool 120 is prevented by abutment of the distal flange 126 with the knob housing 102.

Figure 4:
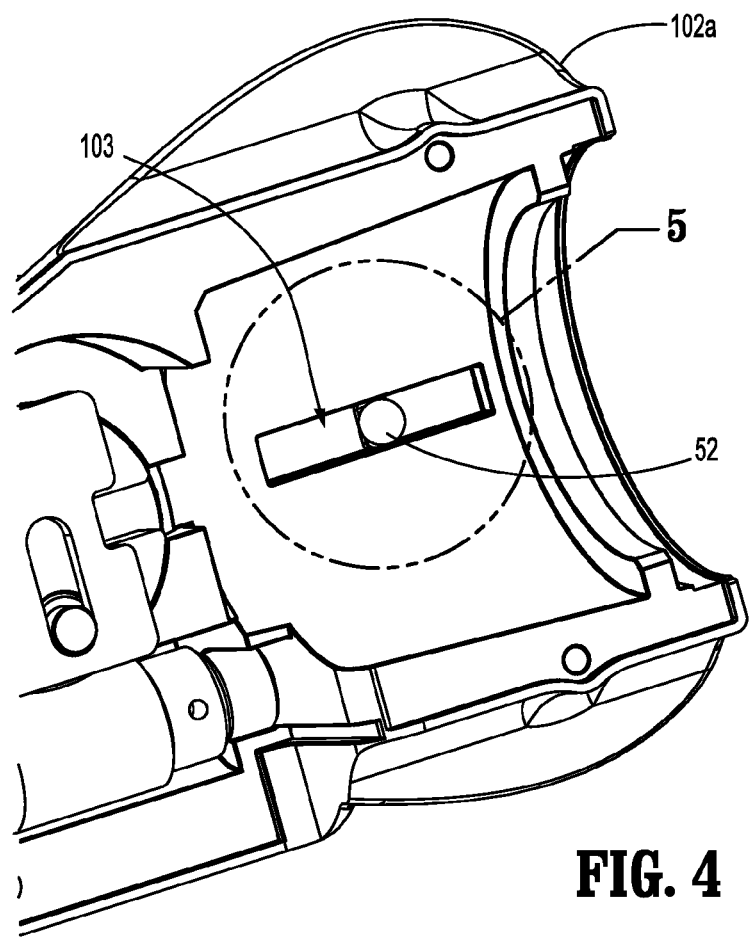
FIG. 4 is a bottom, perspective view of the top articulation dial cover of an articulating neck assembly of the surgical instrument of FIGS. 1-3.
Figure 5:
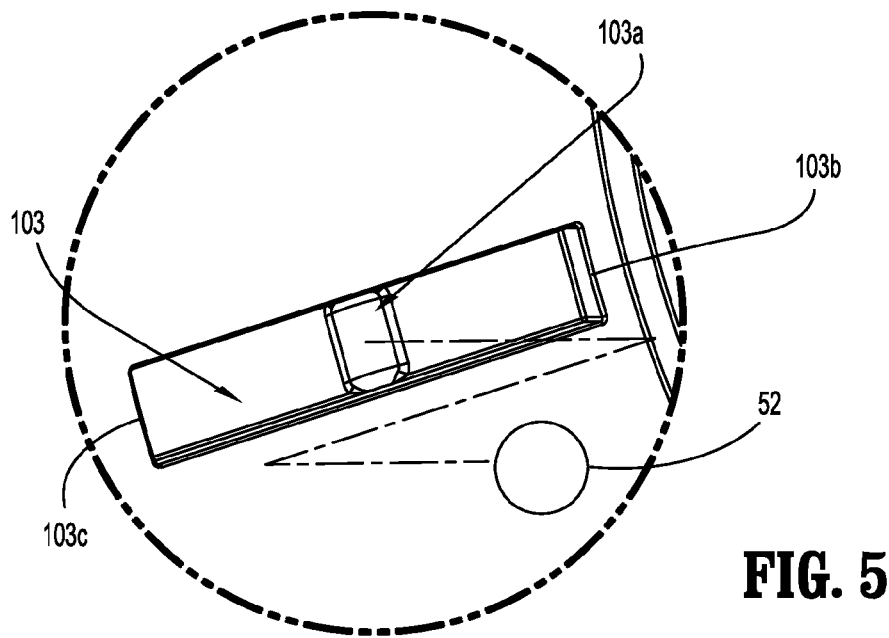
FIG. 5 is a bottom, perspective view of the top articulation dial cover of FIG. 4 with a ball bearing separated therefrom.

As seen in FIGS. 4-6, the surgical instrument 10 includes a rotation limiting mechanism 50 that interacts with the outside of the nose portion 20 and the inside of the knob housing 102. The rotation limiting mechanism 50 includes a ball bearing 52 located within both a longitudinal recess 103, in the upper knob housing half 102a, and a spiral cam slot or helical recess 22 (see FIG. 2), defined about the nose portion 20 of housing 12. The rotation limiting mechanism 50 allows the rotational interface 100 to rotate about the nose portion 20. As shown, rotation limiting mechanism 50 allows the rotational interface 100 to rotate approximately 700°; however other degrees of rotation are envisioned.

With reference to FIGS. 4 and 5, the longitudinal recess 103 defines a neutral detent 103a half way between a proximal end 103b and a distal end 103c of the longitudinal recess 103. The neutral detent 103a provides a tactile indication to the user of a neutral position of the rotational interface 100. The ball bearing 52 travels longitudinally within the longitudinal recess 103 as the knob housing 102 of rotational interface 100 is rotated about the longitudinal 'X' axis. The ball bearing 52 is shown in a neutral position in FIG. 6, a distal most extreme position in FIG. 7, and in a proximal most extreme position in FIG. 8. In use, as the rotational interface 100 is rotated about the nose portion 20, the ball bearing 52 is also rotated about the nose portion 20. The ball bearing 52 rides in the helical recess 22 and is prevented by further travel when ball bearing 52 reaches one of the extreme ends 13b, 103c of longitudinal recess 103 to thereby limit the degree of rotation of knob housing 102 of rotational interface 100. At the extreme ends of the longitudinal recess 103, the ball bearing 52 acts against the ends 103b, 103c thereof to prevent the rotational interface 100 from rotating further with respect to the housing 12.

Figure 11:
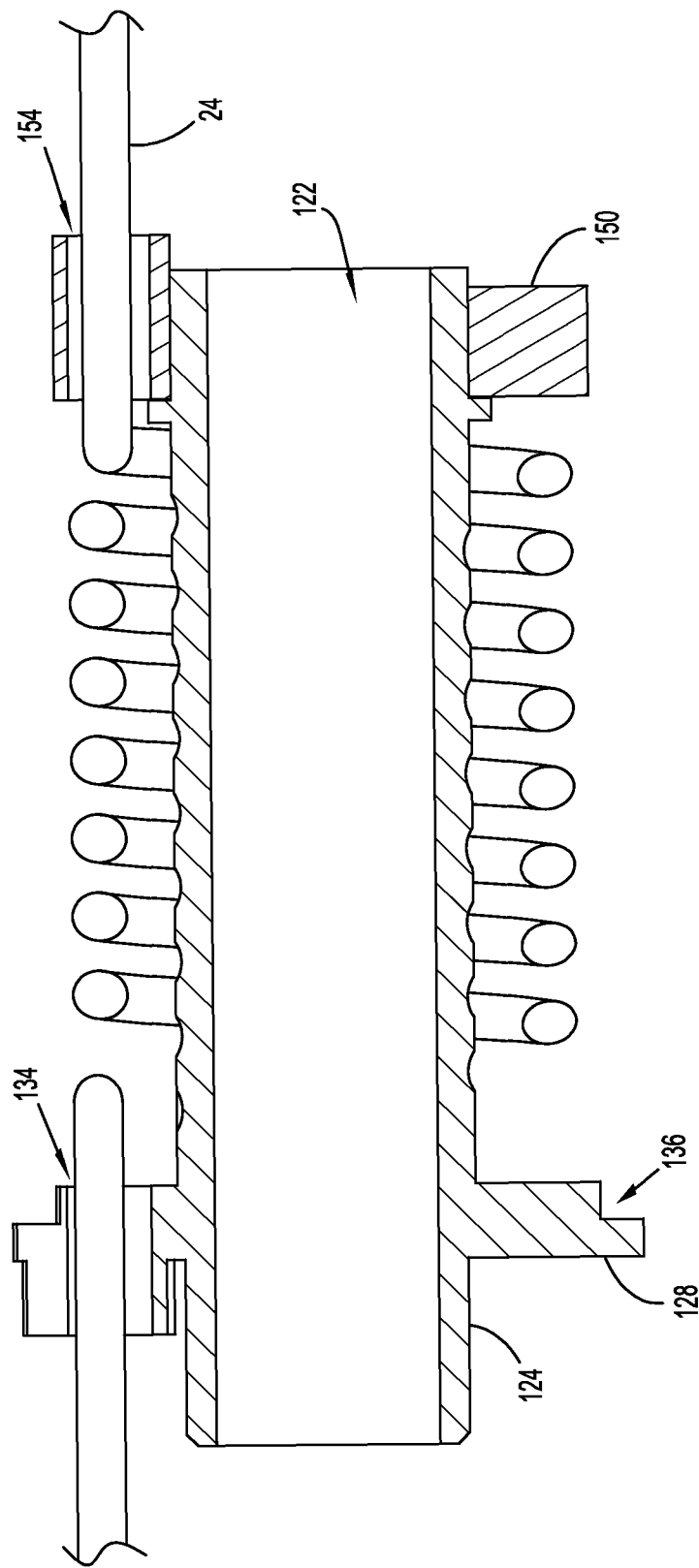
FIG. 11 is a longitudinal, cross-sectional view as taken through 11-11 of FIG. 9, illustrating a neutral state of the wire spool coupling.
Figure 12:
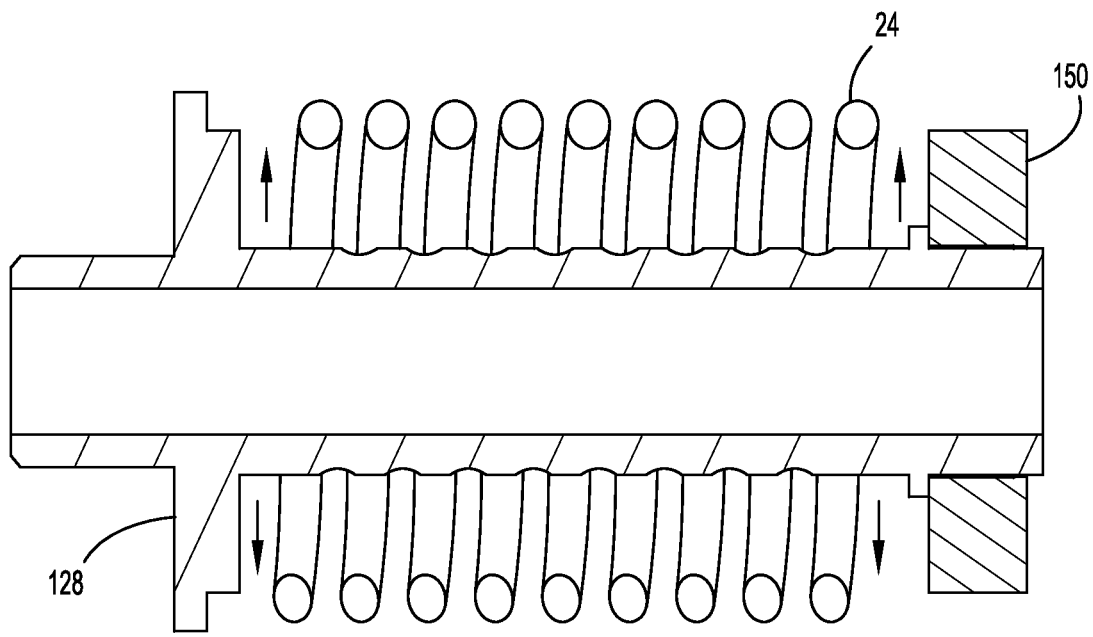
FIG. 12 is a longitudinal, cross-sectional view as taken through 11-11 of FIG. 9, illustrating a first extreme state of the wire spool coupling.
Figure 13:
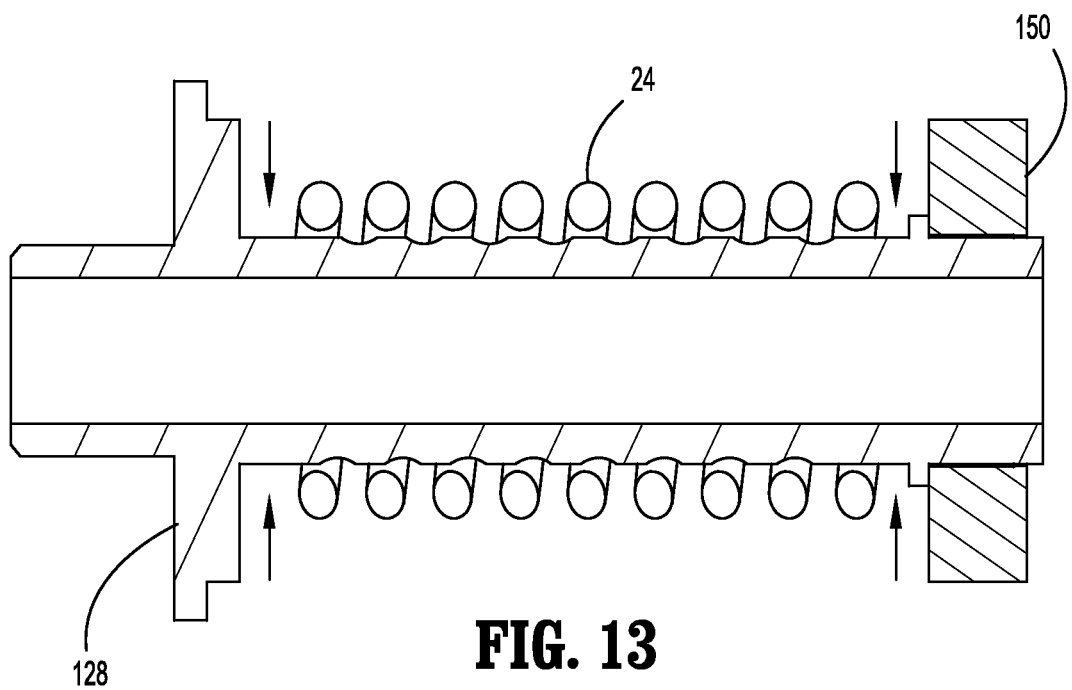
FIG. 13 is a longitudinal, cross-sectional view as taken through 11-11 of FIG. 9, illustrating a second extreme state of the wire spool coupling.

With reference to FIGS. 11-13, the wire 24 is shown in various stages during the rotation process of the rotational interface 100. The wire 24 is relatively loose about the spool 120 when the rotational interface 100 is in a neutral position and the ball bearing 52 is in the neutral detent 103a, as shown in FIG. 6. The wire 24 is unwrapped and is forced radially outward about the spool 120, as shown in FIG. 12, when the rotational interface 100 is rotated in a first direction and the ball bearing 52 is drawn distally. Rotating the rotational interface 100 in a second direction, opposite to the first direction, as shown in FIG. 13, wraps the wire 24 tighter about the spool 120 to draw the wire 24 radially inward toward the spool 120.

The helical recess 130 may provide a predefined path for the wire 24 as the wire 24 is tightened about the spool 120. By adding or subtracting the number of loops of wire 24 wrapping around spool 120 and adjusting the length of the helical and longitudinal recesses; the rotational range of spool 120, knob housing 102, and/or rotational interface 100 can be increased or decreased.

In order to reduce electrical noise emissions and/or susceptibility, it is contemplated that circumferential shielding may be added around wire 24 wrapped around spool 120 and/or wires may be twisted.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure. Therefore, the above description should not be construed as limiting, but merely as exemplifications of embodiments. Those skilled in the art will envision other modifications within the scope and spirit of the present disclosure.

What is claimed is:

1. A surgical apparatus for performance of a surgical procedure on body tissue, the surgical apparatus comprising: a housing; an elongate tubular member at least partially supported by the housing, the elongate tubular member defining a center lumen and a longitudinal axis; a drive assembly extending from the housing into the center lumen of the elongate tubular member; an electrical coupling component being located about the drive assembly; and an electrical wire extending from within the housing into the elongate tubular member, the electrical wire being wrapped about the electrical coupling component, the electrical coupling component allowing the elongate tubular member to rotate about the longitudinal axis while allowing the electrical wire to be fixed within the housing and the elongate tubular member, wherein the electrical coupling component includes a fixed member and a rotatable member, the fixed member is prevented from both longitudinal and rotational movement by the housing, the rotatable member being rotatable with respect to both the fixed member and the housing, wherein the rotatable member includes a tubular spool, the tubular spool defines a helical groove to provide the electrical wire with a predefined path along the tubular spool.

2. The surgical apparatus according to claim 1, further comprising an electrical component connected with the elongate tubular member.

3. The surgical apparatus according to claim 1, further comprising a limiting mechanism to restrict rotational movement of the elongate tubular member.

4. The surgical apparatus according to claim 3, the limiting mechanism includes an inner band and an outer collar and a ball bearing, the inner band defines a spiral cam slot, the outer collar defines a longitudinal cam slot, the ball bearing being located within both the spiral cam slot and the longitudinal cam slot.

5. The surgical apparatus according to claim 4, wherein the spiral cam slot traverses the inner band about 700°.

6. The surgical apparatus according to claim 4, wherein a neutral detent is defined midway along the longitudinal cam slot to provide a tactile indication of a neutral position of the elongate tubular member.

7. The surgical apparatus according to claim 4, wherein the elongate tubular member is prevented from further rotation by the ball bearing acting against either a proximal end or a distal end of the longitudinal cam slot.

8. The surgical apparatus according to claim 1, wherein the fixed member defines a first passageway providing a path for the electrical wire through the fixed member, the rotatable member defines a second passageway providing a path for the electrical wire through the rotatable member.

9. A surgical apparatus for performance of a surgical procedure on body tissue, the surgical apparatus comprising: a housing; an elongate member being rotationally connected with the housing; an electrical coupling interface having a fixed member and a rotatable member, one of the fixed member and the rotatable member having a spool extending therefrom, the spool being in connection with the other of the fixed member and the rotatable member; and a wire having a first portion and a second portion and a third portion, the first portion of the wire being in a fixed position with respect to the housing, the second portion of the wire being wrapped about the spool, the third portion of the wire being restrained with respect to the elongate member, wherein the spool defines a helical groove to provide the electrical wire with a predefined path along the spool.

10. The surgical apparatus according to claim 9, further comprising an electrical component connected with the elongate member.

11. The surgical apparatus according to claim 9, further comprising a limiting mechanism to restrict rotational movement of the elongate member.

12. The surgical apparatus according to claim 11, the limiting mechanism includes an inner band and an outer collar and a ball bearing, the inner band defines a spiral cam slot, the outer collar defines a longitudinal cam slot, the ball bearing being located within the spiral cam slot and the longitudinal cam slot.

13. The surgical apparatus according to claim 12, wherein the spiral cam slot traverses the inner band about 700°.

14. The surgical apparatus according to claim 12, wherein a neutral detent is defined midway along the longitudinal cam slot to provide a tactile indication of a neutral position of the elongate member.

15. The surgical apparatus according to claim 9, wherein the fixed member is prevented from both longitudinal and rotational movement by the housing, the rotatable member being rotatable with respect to both the fixed member and the housing.

16. The surgical apparatus according to claim 9, wherein the fixed member defines a first passageway providing a path for the wire through the fixed member and the rotatable member defines a second passageway providing a path for the wire through the rotatable member.

17. The surgical apparatus according to claim 9, further comprising a drive assembly at least partially supported by the housing, the drive assembly being at least partially positioned within the electrical coupling interface.

18. A surgical apparatus for performance of a surgical procedure on body tissue, the surgical apparatus comprising: a housing; an elongate tubular member at least partially supported by the housing, the elongate tubular member defining a center lumen and a longitudinal axis; a drive assembly extending from the housing into the center lumen of the elongate tubular member; an electrical coupling component being located about the drive assembly; an electrical wire extending from within the housing into the elongate tubular member, the electrical wire being wrapped about the electrical coupling component, the electrical coupling component allowing the elongate tubular member to rotate about the longitudinal axis while allowing the electrical wire to be fixed within the housing and the elongate tubular member; and a limiting mechanism to restrict rotational movement of the elongate tubular member, wherein the limiting mechanism includes an inner band and an outer collar and a ball bearing, the inner band defines a spiral cam slot, the outer collar defines a longitudinal cam slot, the ball bearing being located within both the spiral cam slot and the longitudinal cam slot.

19. A surgical apparatus for performance of a surgical procedure on body tissue, the surgical apparatus comprising: a housing; an elongate member being rotationally connected with the housing; an electrical coupling interface having a fixed member and a rotatable member, one of the fixed member and the rotatable member having a spool extending therefrom, the spool being in connection with the other of the fixed member and the rotatable member; a wire having a first portion and a second portion and a third portion, the first portion of the wire being in a fixed position with respect to the housing, the second portion of the wire being wrapped about the spool, the third portion of the wire being restrained with respect to the elongate member; and a limiting mechanism to restrict rotational movement of the elongate member, wherein the limiting mechanism includes an inner band and an outer collar and a ball bearing, the inner band defines a spiral cam slot, the outer collar defines a longitudinal cam slot, the ball bearing being located within the spiral cam slot and the longitudinal cam slot.

* * * * *